US011885747B2

(12) United States Patent
Davis et al.

(10) Patent No.: US 11,885,747 B2
(45) Date of Patent: Jan. 30, 2024

(54) MODULAR OPTICAL SENSOR

(71) Applicant: Ecolab USA Inc., Saint Paul, MN (US)

(72) Inventors: Brandon Matthew Davis, Oswego, IL (US); Stephen J. Hinterlong, Elburn, IL (US); David Alan Ambrose, St. Charles, IL (US)

(73) Assignee: Ecolab USA Inc., Saint Paul, MN (US)

( * ) Notice: Subject to any disclaimer, the term of this patent is extended or adjusted under 35 U.S.C. 154(b) by 138 days.

(21) Appl. No.: 17/180,373

(22) Filed: Feb. 19, 2021

(65) Prior Publication Data

US 2021/0262942 A1    Aug. 26, 2021

Related U.S. Application Data

(60) Provisional application No. 62/979,874, filed on Feb. 21, 2020.

(51) Int. Cl.
*G01N 21/77* (2006.01)
*G01N 21/64* (2006.01)
(Continued)

(52) U.S. Cl.
CPC ......... *G01N 21/77* (2013.01); *G01N 21/6428* (2013.01); *H05K 1/0274* (2013.01);
(Continued)

(58) Field of Classification Search
CPC ............... G02N 21/6428; G02N 21/77; G02N 2021/7756; G02N 2021/7763;
(Continued)

(56) References Cited

U.S. PATENT DOCUMENTS 4,816,695 A    3/1989 Lavin
4,876,446 A    10/1989 Kambe et al.
(Continued)

FOREIGN PATENT DOCUMENTS

CN    111727365 A  *  9/2020    ............. G01N 15/06
WO       2011107102 A1    9/2011
WO    WO-2018208326 A1  *  11/2018    ............. G01N 21/31

OTHER PUBLICATIONS

International Patent Application No. PCT/US2021/018842, International Search Report and Written Opinion dated May 25, 2021, 15 pages.

*Primary Examiner* — Thomas A Hollweg
*Assistant Examiner* — Mary A El-Shammaa
(74) *Attorney, Agent, or Firm* — Fredrikson & Byron, P.A.

(57) ABSTRACT

An optical sensor may include a housing, a printed circuit board, an optical emitter, and an optical detector. The housing can define a channel configured to receive a transparent tubing line through which fluid can flow during operation. The housing can have multiple optical pathways, including a primary optical pathway transecting the channel, a light emission optical pathway, and a light detection optical pathway. The optical emitter and optical detector can each be mounted on the printed circuit board. Further, the housing may be positioned on the printed circuit board with the optical emitter aligned to emit light into the light emission optical pathway and the optical detector aligned to receive light from the light detection optical pathway.

20 Claims, 5 Drawing Sheets

(51) Int. Cl.
*H05K 1/02* (2006.01)
*H05K 1/18* (2006.01)

(52) U.S. Cl.
CPC ..... *H05K 1/181* (2013.01); *G01N 2021/7763* (2013.01); *H05K 2201/10106* (2013.01); *H05K 2201/10121* (2013.01); *H05K 2201/10151* (2013.01)

(58) Field of Classification Search
CPC .......... H05K 2201/10151; H05K 2201/10121; H05K 2201/10106; H05K 1/181; H05K 1/0274
See application file for complete search history.

(56) References Cited

U.S. PATENT DOCUMENTS

| | | |
|---|---|---|
| 5,672,887 A | 9/1997 | Shaw et al. |
| 6,043,893 A | 3/2000 | Treiman et al. |
| 6,157,454 A | 12/2000 | Wagner et al. |
| 9,322,773 B2 | 4/2016 | Coates et al. |
| 9,818,669 B2 | 11/2017 | Jones et al. |
| 10,088,410 B2 | 10/2018 | Egalon |
| 2009/0097029 A1 | 4/2009 | Tokhtuev et al. |
| 2015/0090900 A1 | 4/2015 | Banks et al. |
| 2016/0266044 A1* | 9/2016 | Ribitsch ................ G01J 3/0272 |
| 2020/0200673 A1* | 6/2020 | Coates .................. G01N 21/85 |

* cited by examiner

MODULAR OPTICAL SENSOR

RELATED MATTERS

This application claims the benefit of U.S. Provisional Patent Application No. 62/979,874, filed Feb. 21, 2020, the contents of which are incorporated herein by reference.

TECHNICAL FIELD

This disclosure relates to optical sensors and techniques utilizing optical sensors.

BACKGROUND

Optical sensors are used in many fields to measure process and environmental conditions. An optical sensor can be used to optically interrogate a sample having an unknown concentration of one or more constituents of interest, allowing the concentration of those constituents to be determined based on the optical response of the sample. For example, in chemical and process industries involving bulk flows of liquids and gases, optical sensors can be deployed to measure the conditions and/or composition of the flowing streams. This can provide operational insights to the operator of such processes, allowing the operating conditions of the process to be modified and/or the addition of one or more chemical agents to the process to be controlled based on the measurement information provided by the optical sensor.

In an idealized scenario, an optical sensor may be utilized in any system and at any point in a process where measurement information is desired to be available by a user. As more sensors are utilized in a process, the volume of control information provided to the user increases proportionally. This can provide more granular data insights to the user, potentially allowing quicker and more accurate control actions based on the measurement data.

In practice, however, the cost and complexity of many optical sensors limit the applications where the optical sensors can be economically deployed. Optical sensors are typically designed with high precision optical and electronic components, resulting in comparatively expensive devices that are selectively deployed. As a result, systems and processes that may benefit from accurate measurement information provided by one or more optical sensors are implemented without such sensors to avoid the cost and complexity of such sensors.

SUMMARY

In general, this disclosure is directed to optical sensor devices along with associated systems and techniques. In some examples, an optical sensor is configured as a modular unit that has a housing through which a transparent tubing line extends. The housing can provide a primary optical pathway transecting the transparent tubing line. The housing may be positioned on a printed circuit board carrying an optical emitter and an optical detector. The optical emitter can emit light into an emission optical pathway that intersects the primary optical pathway. The optical detector can receive light from a light detection optical pathway that also intersects the primary optical pathway, e.g., on an opposite side of the transparent tubing line. In operation, the optical emitter can emit light that is directed via optical pathways of the housing through sample flowing through the transparent tubing line, resulting in light emission (e.g., transmittance, scattering, fluorescence) on the opposite side of the transparent tubing line that can be detected via the optical detector also via optical pathways of the housing.

An optical sensor according to the disclosure may provide a compact, low-cost construction that allows the optical sensor to be readily deployed in various different applications. In some implementations, for example, the optical sensor may be fabricated using readily available light emitting diode(s) and photodetector(s) that are surface mounted to a printed circuit board along with other surface mounted components such as resistors, capacitors and/or other integrated circuit components to provide electronics of the optical sensor. The optical sensor housing can be efficiently produced, for example using molding, casting, and/or 3-D printing techniques, and positioned on the printed circuit board over the mounted light emitting diode(s) and photodetector(s). The transparent tubing line may then be inserted into and/or through the housing to provide a fluid communication pathway for receiving a sample for optical analysis from outside of the sensor and delivering the sample to the optical sensor. In this way, the optical sensor can be efficiently produced, expanding the number of applications where the optical sensor can be deployed in commercial practice.

Although an optical sensor according to disclosure can have a variety of different design configurations as discussed herein, in some examples, the optical sensor is deployed as part of a system that includes multiple optical sensor elements. Each optical sensor element can have a printed circuit board carrying an optical emitter and an optical detector with a housing defining optical pathways positioned over the circuit board to optically couple the emitter and detector to a transparent tubing line running through the housing. The printed circuit board of each optical sensor element may be permanently or removably coupled to a main circuit board carrying one or more processors configured to execute non-transitory computer readable instructions stored in memory for controlling the optical sensor system. For example, the one or more processors on the main circuit board may control the optical emitters and detectors of the individual optical sensor elements to make optical measurements on the sample in the transparent tubing line.

In some configurations of the optical sensor system, the individual optical sensor elements may be selectively attachable to and detachable from the main printed circuit board (e.g., without breaking permanent bonds or connections, such as solder bonds, wiring, and/or other permanently joined physical and/or electrical connections). When so configured, the optical sensor system may include multiple different individual optical sensor elements, each of which has a different configuration (e.g., an optical emitter that emits at a different wavelength) than each other optical sensor element. As a result, an operator of the optical sensor system may select one of multiple different individual optical sensor elements for an intended application and engage that selected optical sensor element with the main printed circuit board. The operator can further route the transparent tubing line through the selected optical sensor element. In this manner, the optical sensor system can provide an interchangeable series of different optical sensor elements that can be exchanged in and out of the system depending on the needs and configuration of the user. Each individual optical sensor element may be a comparatively low cost component that can be engaged with the more expensive main circuit board and processing hardware.

In one example, an optical sensor is described that includes a housing, a printed circuit board, an optical emitter, and an optical detector. The housing defines a channel configured to receive a transparent tubing line through which fluid can flow during operation. The housing also defines a primary optical pathway transecting the channel, a light emission optical pathway intersecting the primary optical pathway on one side of the channel, and a light detection optical pathway intersecting the primary optical pathway on an opposite side of the channel. The optical emitter is mounted on the printed circuit board, and the optical detector is mounted on the printed circuit board. The example specifies that the housing is positioned on the printed circuit board with the optical emitter aligned to emit light into the light emission optical pathway and the optical detector is aligned to receive light from the light detection optical pathway.

In another example, an optical sensor system is described. The system includes a main printed circuit board carrying a processor and a plurality of optical sensors. Each of the plurality of optical sensors a housing, a printed circuit board, an optical emitter, and an optical detector. The housing defines a channel configured to receive a transparent tubing line through which fluid can flow during operation. The housing also defines a primary optical pathway transecting the channel, a light emission optical pathway intersecting the primary optical pathway on one side of the channel, and a light detection optical pathway intersecting the primary optical pathway on an opposite side of the channel. The optical emitter is mounted on the printed circuit board, and the optical detector is mounted on the printed circuit board. The example specifies that the housing is positioned on the printed circuit board with the optical emitter aligned to emit light into the light emission optical pathway and the optical detector is aligned to receive light from the light detection optical pathway. In addition, the example states that the printed circuit boards of the plurality of optical sensors in the system are coupled to the main circuit board. The processor carried by the main circuit board is electrically coupled to the optical emitter and optical detector of each of the plurality of optical sensors. The processor can be configured to control the optical emitter and optical detector of each of the plurality of optical sensors.

In another example, a method is described. The method involves flowing a sample through a fluid tubing line extending through a plurality of optical sensors coupled to a main printed circuit board carrying a processor. The method specifies that each of the plurality of optical sensors includes a housing, a printed circuit board, an optical emitter, and an optical detector. The housing defines a channel in which the fluid tubing line is positioned, a primary optical pathway transecting the channel, a light emission optical pathway intersecting the primary optical pathway, and a light detection optical pathway intersecting the primary optical pathway on an opposite side of the channel. The printed circuit board is coupled to the main printed circuit board. The optical emitter is mounted on the printed circuit board. The optical detector is mounted on the printed circuit board. The method involves controlling, by the processor, the optical emitter of each of the plurality of optical sensors to emit light into the sample via the light emission optical pathway and the primary optical pathway. The method also involves controlling, by the processor, the optical detector of each of the plurality of optical sensors to detect light from the sample via the primary optical pathway and the light detection optical pathway.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the disclosure. Rather, the following description provides some practical illustrations for implementing examples of the present disclosure. Examples of constructions, materials, dimensions, and manufacturing processes are provided for selected elements, and all other elements employ that which is known to those of ordinary skill in the field. Those skilled in the art will recognize that many of the noted examples have a variety of suitable alternatives.

Optical sensors are used in a variety of applications, including monitoring industrial processes. An optical sensor can be implemented as a portable, hand-held device that is used to periodically analyze the optical characteristics of a fluid in an industrial process. Alternatively, an optical sensor can be installed online to continuously analyze the optical characteristics of a fluid in an industrial process. In either case, the optical sensor may optically analyze the fluid sample and determine different characteristics of the fluid, such as the concentration of one or more chemical species in the fluid.

For example, an optical sensor can be used to monitor the characteristics of water flowing through a piping system in a variety of different industrial applications. Example waters that may be measured using an optical sensor include, but are not limited to: heating water systems (e.g., boiler systems), cooling water systems (e.g., systems comprising a cooling tower), pipelines for water transport (e.g., seawater transport, which may be in transport to mining operations), waste water systems (e.g., industrial waste water streams, including those in the petrochemical and mining industries), water carrying cleaning and/or sanitizing chemicals, and the like. Either continuously or on an intermittent basis, samples of water can be extracted from the piping system and delivered to the optical sensor. Within the optical sensor, light is emitted into the water sample and used to evaluate the characteristics of the water sample. The optical sensor may determine a concentration of one or more chemical components in the water sample. Measurement information from the optical sensor concerning the concentration of the one or more chemical components can then be used to control the water system and/or the introduction of one or more chemical agents into the water system.

While an optical sensor according to the disclosure can have a variety of different configurations, in some examples, the optical sensor is designed with a printed circuit board carrying an optical emitter and an optical detector. A housing is positioned on the board with emitter and detector optical pathways of the housing aligned with the optical emitter and optical detector on the circuit board, respectively. The housing can also define a cutout into which a transparent tubing line is positioned. The cutout, and transparent tubing line positioned therein, can be transected by an optical pathway of the housing that provides optical communication to the optical emitter on one side of the tubing line and to the optical detector on another side of the tubing line.

Figure 1:
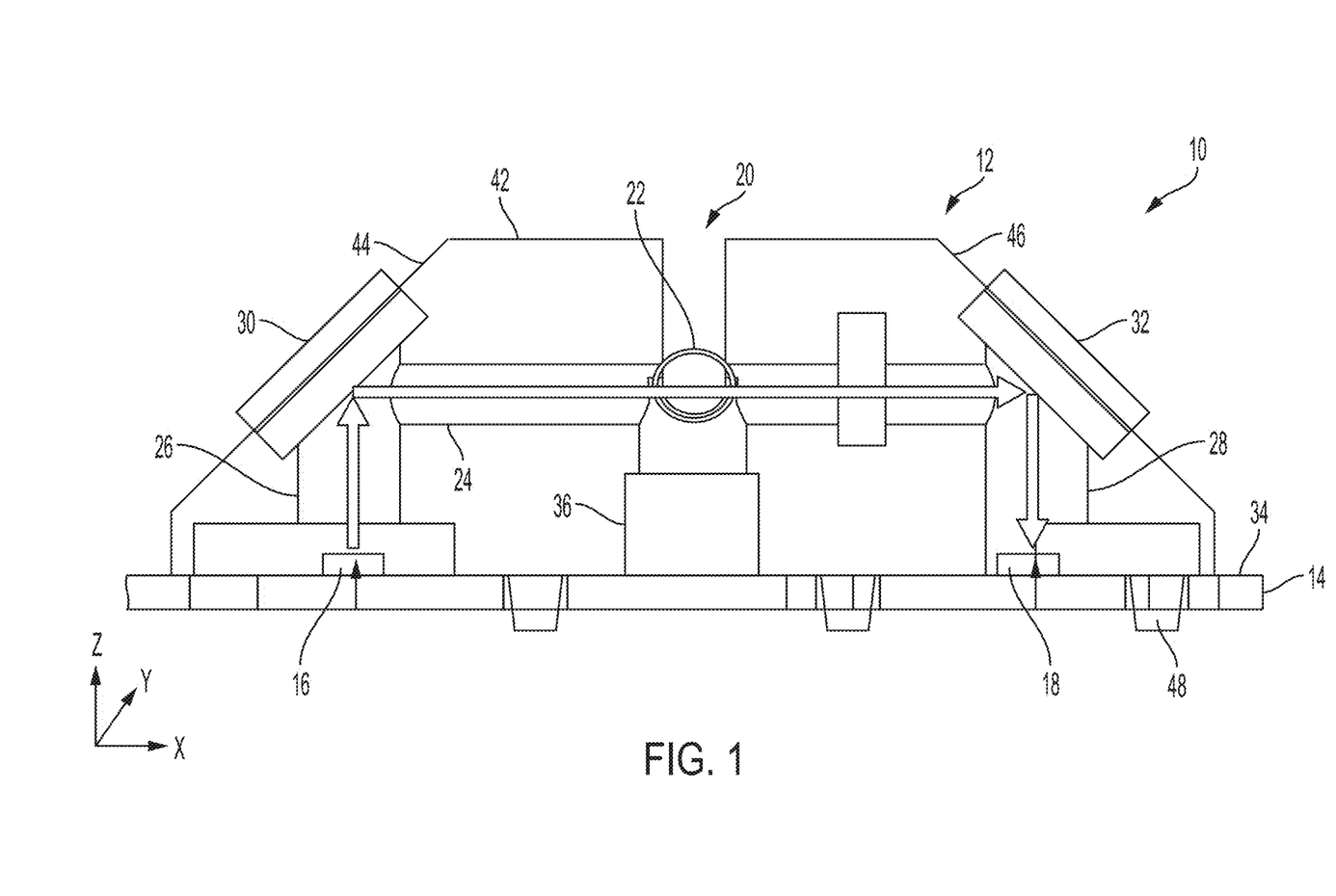
FIGS. 1 and 2 are side and perspective views, respectively, of an example optical sensor.
Figure 2:
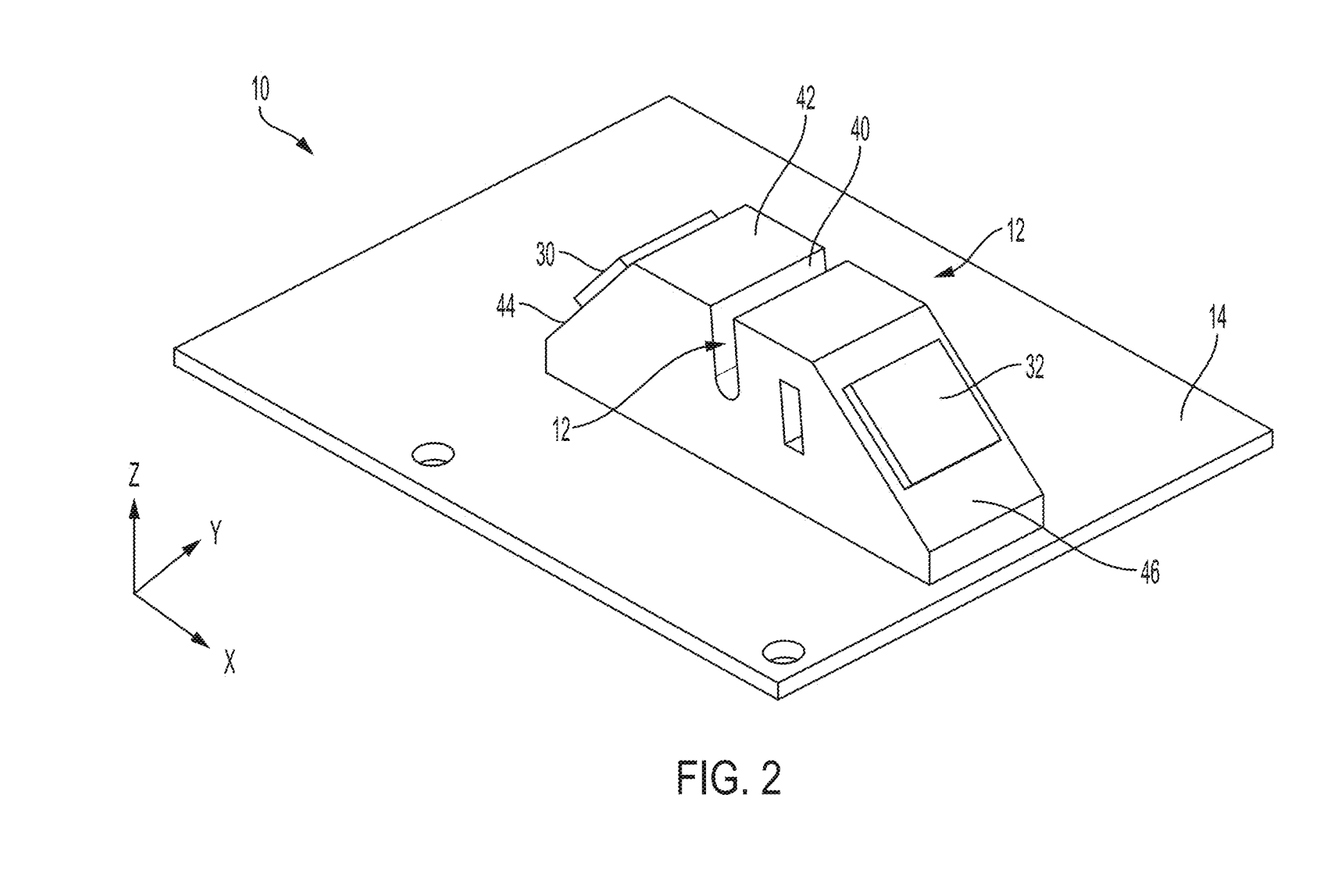

FIGS. 1 and 2 are side and perspective views, respectively, of an example optical sensor 10. In the illustrated example, sensor 10 includes a housing 12 positioned on a circuit board 14. Circuit board 14 carries at least one optical emitter 16 and at least one optical detector 18. Housing 12 can define one or more optical pathways that guide light from optical emitter 16 to a sample for analysis and that guide light from the sample to optical detector 18 for detection. Optical sensor 10 can be used to measure an optical characteristic of any desired fluid subject to analysis.

To receive a sample for analysis, optical sensor 10 may include an optically transparent sample receiving area that can be exposed to light emitted by optical emitter 16. In the example of FIGS. 1 and 2, housing 12 of optical sensor 10 includes a channel 20 configured to receive a transparent tubing line 22 in the channel. Transparent tubing line 22 can provide a fluid conduit through which a fluid to be subject to optical analysis can flow. In some implementations, the fluid subject to optical analysis may flow through transparent tubing line 22 while being optically analyzed (e.g., without stopping in the optical sensor for analysis). In other implementations, the fluid subject to optical analysis may be conveyed into the optical sensor via transparent tubing line 22 and held statically in the tubing line for a period of time sufficient to optically analyze the fluid.

In either case, housing 12 of optical sensor 10 may define a primary optical pathway 24 transecting channel 20. Primary optical pathway 24 may be configured (e.g., sized, shaped, and/or positioned) such that when transparent tubing line 22 is positioned within channel 20, light directed through the primary optical pathway intersects the transparent tubing line in any fluid therein. For example, primary optical pathway 24 may be arranged relative to channel 20 such that, when transparent tubing line 22 is inserted fully into the channel (e.g., in the negative Z-direction indicated on FIG. 1), the primary optical pathway cuts across the transparent tubing line. In some examples, primary optical pathway 24 is arranged relative to channel 20 and/or transparent tubing line 22 positioned in the channel such that a geometric center of the primary optical pathway (e.g., in the Y-Z plane indicated on FIG. 1) is substantially aligned with and/or coplanar with a geometric center of the region of channel 20 where transparent tubing line 22 is intended to be inserted and/or the transparent tubing line so inserted (e.g., also in the Y-Z plane indicated on FIG. 1).

Optical sensor 10 can include any suitable number of optical pathways optically connecting various emitter and detector components housed inside the housing 12 to the fluid sample under analysis in transparent tubing line 22. In the example of FIG. 1, optical sensor 10 is illustrated as having a first optical pathway 26, which can be referred to as a light emission optical pathway. Optical sensor 10 is also illustrated as having a second optical pathway 28, which can be referred to as a light detection optical pathway.

Light emission optical pathway 26 can be optically connected to optical emitter 16 and primary optical pathway 24. Light emission optical pathway 26 can guide light emitted by optical emitter 16 to primary optical pathway 24 which, in turn, can guide the light to transparent tubing line 22 and any fluid contained therein. Primary optical pathway 24 can guide light received from transparent tubing line 22 and any fluid contained therein to light detection optical pathway 28 which, in turn, can guide the light to optical detector 18.

Optical pathways in optical sensor 10 may be channels, segments of optically conductive tubing (e.g., fiber optic lines), or ducts that allow light to be conveyed through the optical sensor. The optical pathways may also be formed (e.g., machined, cast, 3-D printed) into housing 12 of the optical sensor. For example, the optical pathways may define bounded channels, tubes, conduits, or cavities in housing 12 that control light movement through the sensor. In different examples, the optical pathways may or may not be surrounded by optically opaque material, e.g., to bound light movement through the optical pathways and to prevent light from escaping through the sides of the optical pathways. When optical sensor 10 includes multiple optical pathways, the intersection of one optical pathway with another optical pathway may be defined where light traveling linearly through the one optical pathway is required to change direction to travel through the other optical pathway.

Each optical pathway in optical sensor 10 may be the same size (e.g., diameter), or at least one optical pathway may have a different size and at least one other optical pathway. Accordingly, although optical pathway 24 is referred to as a primary optical pathway, it should be appreciated that the primary optical pathway can but need not have a different size than the light emission optical pathway 26 and/or the light detection optical pathway 28. Moreover, while the optical pathways in optical sensor 10 may typically have a circular cross-sectional shape, any one or more of the optical pathways may define any arcuate (e.g., circular, elliptical) or polygonal (e.g., square, rectangular) cross-sectional shape.

Optical sensor 10 can have a number of different optical pathway configurations and the configurations can vary, e.g., based on the number of optical emitters and detectors contained in the sensor. Where optical sensor 10 includes one optical pathway intersecting another optical pathway to redirect the direction of light movement through housing 12, a mirror element can be positioned at the intersection. Each mirror element can be configured to reflect light and can be positioned at a location appropriate to redirect light from one optical pathway to another optical pathway.

In the example of FIG. 1, optical sensor 10 is illustrated as having a first mirror element 30 and a second mirror element 32. First mirror element 30 is positioned at an intersection between light emission optical pathway 26 and primary optical pathway 24. First mirror element 30 can reflect light emitted by optical emitter 16 and directed through light emission optical pathway 26 into primary optical pathway 24. Second mirror element 32 is positioned at an intersection between light detection optical pathway 28 and primary optical pathway 24. Second mirror element 32 can reflect the light received from the fluid sample into primary optical pathway 24 from the primary optical pathway into light detection optical pathway 28. Light detection optical pathway 28 can direct that light to optical detector 18.

Each feature described as a mirror in optical sensor 10 may be partially (e.g., greater than 40%, such as greater than 50%, or greater than 90%) reflective to the wavelengths intended to be emitted and/or detected in the optical sensor. In some implementations, a mirror may be formed of a glass substrate coated with an optical coating, such as a dichroic optical coating. Such a coating may be a series of coated layers that form reflective cavities that resonate with desired wavelengths.

In other implementations, a mirror may be formed from a polymeric substrate carrying a mirror coating. Example polymeric substrates that may be used include, but are not limited to: acrylic substrates, PET substrates, and polystyrene substrates. The mirror coating may be aluminum, silver, and/or other reflective material. Each mirror in optical sensor 10 may have the same construction or different mirrors may be fabricated from different materials. In some examples, optical sensor 10 is constructed using mirrors formed of polymeric substrates coated with a non-precious metal reflective coating, which can provide a durable and economical construction.

Light emission optical pathway 26 and light detection optical pathway 28 can each intersect primary optical pathway 24 at any suitable angles. Likewise, primary optical pathway 24 can extend at any desired direction through housing 12. In the illustrated example of FIG. 1, primary optical pathway 24 is illustrated as extending in a direction parallel to a top surface 34 of circuit board 14. Light emission optical pathway 26 is illustrated as extending approximately orthogonally (approximately at 90°) from the primary optical pathway 24 to the circuit board 14. Light detection optical pathway 28 is also illustrated as extending approximately orthogonally (approximately 90°) from the primary optical pathway 24 to the circuit board 14. When light emission optical pathway 26 and light detection optical pathway 28 intersect primary optical pathway 24 at approximately 90° angles, first mirror 30 and second mirror 32 may be oriented at approximately 45° angles, e.g., relative to the direction of light traveling through primary optical pathway 24. In some examples, an intersection between one optical pathway and another optical pathway (e.g., between light emission optical pathway 26 and primary optical pathway 24 and/or between light detection optical pathway 28 and primary optical pathway 24) is defined by a bend. The bend may be defined by a sharp angle or a radius of curvature. In either case, the bend may be formed by one or more segments or lumens. For example, a single lumen having a bend formed therein may form at least a portion of one optical pathway, at least a portion of the intersecting optical pathway, and the intersection therebetween.

Optical sensor 10 includes one or more light sources which, in the illustrated example, is shown with a single light source: optical emitter 16. Optical emitter 16 can be implemented using any appropriate light source, such as a laser, a lamp, an LED, or the like. In some examples, optical emitter 16 is configured to emit light at a single wavelength or narrow range of wavelengths. In other examples, optical emitter 16 is configured to emit light over a wide range of wavelengths.

For example, as discussed in greater detail below with respect to FIG. 3, optical sensor 10 may be implemented in a broader system that includes multiple sensors. Each sensor may include an optical emitter that emits at a different wavelength and/or different wavelength range than the optical emitter in each other sensor (with the wavelength range of one sensor optionally overlapping with the wavelength range in another sensor). For example, optical emitter 16 of one optical sensor 10 may be configured to emit light within a first range of wavelengths to generate fluorescent emissions within the fluid sample. The optical emitter 16 of a second optical sensor 10 may then be configured to emit light within a second range of wavelengths different than the first range of wavelengths to measure the amount of light scattered by the fluid sample.

To detect the light received from the fluid sample under analysis, optical sensor 10 includes one or more optical detectors 18 which, in the illustrated example, is shown as a single optical detector 18. Each optical detector 18 can be implemented using any appropriate detector for detecting light, such as a solid-state photodiode or photomultiplier, for example. Optical detector 18 may be sensitive to, and therefore detect, only a narrow band of wavelengths. Alternatively, the optical detector 18 may be sensitive to, and therefore detect, a wide range of light wavelengths.

Optical emitter 16 and optical detector 18 can be mechanically and/or electrically coupled to circuit board 14 using any suitable mounting techniques. For example, optical emitter 16 and optical detector 18 may be mounted to circuit board 14 using through hole technology in which leads of the respective components are inserted through holes on one side of the board and soldered onto copper traces on the other side of the board. As another example, optical emitter 16 and optical detector 18 may be mounted to circuit board 14 using surface-mount technology, thereby providing surface-mounted components. Surface-mount technology generally involves placing a surface-mount device (e.g., optical emitter 16, optical detector 18) directly on the surface of circuit board 14 (e.g., on solder pads of the circuit board) and reflowing the solder to electrically and mechanically coupled components to the circuit board.

To control the wavelengths of light emitted by optical emitters 16 and/or detected by the optical detector 18 in sensor 10, the optical sensor may include one or more optical filters. For example, optical sensor 10 may include an emission optical filter positioned between optical emitter 16 and transparent tubing line 22 that filters out the wavelengths of light received by the sample in the tubing line. Additionally or alternatively, optical sensor 10 may include a detection optical filter positioned between transparent tubing line 22 and optical detector 18 that filters out the wavelengths of light received from the sample and detected by optical detector 18.

When configured with one or more optical filters, housing 12 of optical sensor 10 may define corresponding cavities in which the one or more optical filter elements can be inserted. The optical filter receiving cavity defined by housing 12 may be positioned at a location that causes the optical filter, once inserted into the filter receiving cavity, to be positioned across the optical pathway to be filtered. In the example of FIG. 1, housing 12 is illustrated as defining an optical filter receiving cavity 36 into which an optical detection filter can be inserted. Additional and/or different optical filter receiving cavities can be formed in housing 12 (e.g., at a different location within the housing). Further, in some implementations, the optical sensor does not include any optical filters (with first mirror 30 and second mirror 32 not being considered an optical filter for purposes of this discussion).

Optical emitter 16 can be configured to emit light at any chosen wavelength or wavelength band (encompassing multiple wavelengths). The specific wavelength(s) at which optical emitter 16 emits light may be selected based on the chemical characteristics of the fluid intended to be detected using sensor 10 and/or the type of optical analysis to be performed. In different applications, sensor 10 may function to measure light scattering from the fluid sample under analysis, fluorescence of the fluid sample under analysis, and/or transmission/absorbance of the fluid sample under analysis.

Although the wavelengths can vary, in some examples, optical emitter 16 is configured to emit light within a wavelength ranging from approximately 225 nanometers (nm) to approximately 700 nm, such as from approximately 250 nm to approximately 350 nm, or from approximately 265 nm to approximately 290 nm. In one implementation, optical emitter 16 emits light within the visible light spectrum. In another implementation, optical emitter can emit light within the ultraviolet (UV) spectrum. In an additional implementation, optical emitter 16 can emit light within the infrared (IR) spectrum. Other wavelengths are both contemplated and possible, and it should be appreciated that the disclosure is not limited in this respect.

To detect light emanating from the fluid sample under analysis (e.g., fluorescent emissions, light scattering, light transmission), sensor 10 in FIG. 1 further includes optical detector 18. Optical detector 18 is optically connected to light detection optical pathway 28 and may receive at least a portion of the light from the fluid sample under analysis (e.g., fluorescent emissions, scattered light, and/or transmitted light).

While sensor 10 in the example of FIG. 1 is illustrated as having only a single optical emitter 16 and a single optical detector 18, the sensor may be constructed with multiple optical emitters and/or multiple optical detectors, each of which are optically connected with transparent tubing line 22 via one or more optical pathways. For example, sensor 10 in FIG. 1 is illustrated as including a second light detection optical pathway 36. Second light detection optical pathway 36 is illustrated as extending approximately orthogonally (approximately 90°) from the primary optical pathway 24 to the circuit board 14. In particular, second light detection optical pathway 36 is illustrated as extending vertically downwardly (in the negative Z-direction) from primary optical pathway 24 where the primary optical pathway transects channel 20. When used, a second optical detector (e.g., configured as described above with respect optical detector 18) can be mounted to printed circuit board 14 with second optical detector pathway 36 position over the second optical detector.

Configuring sensor 10 with a second optical detector and second optical detector pathway 36 may be useful to measured different optical responses of the fluid sample under analysis. For example, first optical detector 18 may be used to measure a transmittance/absorbance of the fluid sample under analysis. A second optical detector associated with second optical detector pathway 36 may be used to measure light scattering (e.g., occurring at a same wavelength or wavelength band that is measured by optical detector 18 to detect transmittance/absorbance) or fluorescence (e.g., occurring at a different wavelength or wavelength band, optionally a longer wavelength, that is measured by optical detector 18 to detect transmittance/absorbance).

As noted, a different number and/or arrangement of light emission optical pathway(s) and/or light detection optical pathway(s) can be used in sensor 10. As one example, sensor 10 may have a single light detection optical pathway arranged as shown by light detection optical pathway 36. When so configured, sensor 10 may omit second mirror 32. As another example, although optical emitter 16 and optical detector 18 are illustrated as being on generally opposite sides of transparent tubing line 22, in other implementations, the optical emitter and optical detector may be on a same side of the transparent tubing line. In these applications, optical detector 18 may detect the light reflected from fluid in the transparent tubing line 22 in a generally opposite direction from a direction light emitter 16 emits light into the fluid.

As mentioned above, sensor 10 can include a channel 20 configured to receive transparent tubing line 22. In the illustrated configuration of FIGS. 1 and 2, channel 20 defines a recess accessible through a top surface of housing 12 defined by a bottom wall 38 (FIG. 2) an opposed sidewalls 40. Transparent tubing line 22 can be inserted vertically downwardly into channel 20, e.g., until a bottom surface of the tubing line contacts bottom wall 38. Channel 20 may have a depth (in the Z-direction) equal to or greater than a major cross-sectional size (e.g., diameter) of transparent tubing line 22. For example, channel 20 may have a depth at least 1.5 times an outer diameter of transparent tubing line 22, such as at least two times an outer diameter of the transparent tubing line. Although channel 20 is illustrated as being bound on three sides by bottom wall 38 and opposed sidewalls 40, the channel may be surrounded about its perimeter by sections of material forming housing 12 (e.g., with housing 12 covering a top surface, a bottom surface, and side surfaces of the tubing line). When so configured, channel 20 may be an opening formed through at least a portion of the cross-section of housing 12 (e.g., in the Y-direction indicate on FIGS. 1 and 2) and, optionally, entirely through the cross-section of the housing.

Transparent tubing line 22 can be positioned in channel 20. Transparent tubing line 22 can be implemented using any type of flexible or inflexible tubing, piping, or conduit. Example materials that may be used to form transparent tubing line 22 include glass and polymeric materials (e.g., polyethylene, polypropylene, polystyrene). The material or materials used to fabricate transparent tubing line 22 may be sufficiently transparent to wavelengths of light emitted into fluid in the tubing line and light to be detected from the fluid in the tubing line so as to effectuate the functions of sensor 10 described herein. Transparent tubing line 22 may be transparent to optical interrogation by optical emitter 16 and optical detector 18 along its entire length or may be an optically transparent section positionable in channel 20 that is in fluid communication with (e.g., coupled to) one or more sections of tubing line that are not optically transparent (e.g., upstream and/or downstream of the section transected by primary optical pathway 24.

In some configurations, transparent tubing line 22 is contained entirely within housing 12 of sensor 10 and is in fluid communication with a source of fluid to be optically analyzed via one or more other tubing lines. In other examples, transparent tubing line 22 may extend from a source of fluid to be optically analyzed by sensor 10 (e.g., an outlet of a pump and/or pumping manifold supplying fluid to be optically analyzed) two and through channel 20 of housing 12. Transparent tubing line 22 may further extend out of channel 20 of housing 12 to a discharge location (e.g., a drain, return line, or other disposal location for dispensing fluid having undergone optical analysis by sensor 10).

For example, optical sensor 10 may be deployed as part of a system that includes multiple optical sensor elements (e.g., each configured as described above with respect to optical sensor 10). Each optical sensor element can have a printed circuit board carrying an optical emitter and an optical detector, with a housing defining optical pathways positioned over the circuit board to optically couple the emitter and detector to a transparent tubing line running through the housing. Transparent tubing line 22 can extend through the channels 20 of each of the multiple optical sensor elements 10, allowing fluid to flow for optical analysis from one sensor 10 to another sensor 10 without exiting the tubing line. In some such implementations, the channels 20 of each of the multiple optical sensor elements 10 can be co-linearly aligned.

Housing 12 of optical sensor 10 can be formed of any suitable material or combination materials, such as metal, a polymeric material, and/or a ceramic material. Housing 12 can be efficiently produced, for example using molding, casting, and/or 3-D printing. For instance, in one specific example, housing 12 is produced from a polymeric material using 3-D printing techniques, allowing the housing to be quickly and cost-effectively produced.

Housing 12 can have a variety of different shapes, which may depend on the number and configuration of optical components included as part of sensor 10. In the example of FIGS. 1 and 2, housing 12 defines a trapezoidal shape that includes a top surface 42, a first lateral side surface 44, and a second lateral side surface 46. First mirror 30 is bonded in an opening formed in the first lateral side surface 44. Second mirror 32 is bonded in an opening formed in the second lateral side surface 46. The mirrors may be bonded (e.g., fixedly connected) to the respective surfaces using an adhesive, melt bonding, frictional fit engagement, and/or mechanical engagement features to retain the mirror to a specific lateral side surface. When configured as illustrated, channel 20 extends through the top surface 42 of housing 12 toward printed circuit board 14 (e.g., bisecting the top surface).

Housing 12 of optical sensor 10 is positioned over printed circuit board 14. In various examples, printed circuit board 14 may be installed inside of housing 12 and/or housing 12 may be affixed to the printed circuit board (e.g., using any of the example bonding techniques discussed above). In still further examples, housing 12 may be positionable on or over printed circuit board 14 without being physically connected to the printed circuit board (e.g., such that the housing is separable from the printed circuit board without breaking any bonds or interconnections between the two components).

Printed circuit board 14 can be formed of one or more flat sheets of insulating material and layers of copper foil laminated together. Chemical etching can divide the copper into separate conducting lines called tracks or circuit traces, pads for connections, vias to pass connections between layers of copper, and/or features such as solid conductive areas for electromagnetic shielding or other purposes. The traces can function as wires fixed in place, and can be insulated from each other by air and the board substrate material. The surface of the printed circuit board 14 may have a coating that protects the copper from corrosion and reduces the chances of solder shorts between traces or undesired electrical contact with stray bare wires. This coating can be called a solder resist or solder mask because it can function to help prevent solder shorts.

Printed circuit board 14 can be single-sided (one copper layer), double-sided (two copper layers on both sides of one substrate layer), or multi-layer (outer and inner layers of copper, alternating with layers of substrate). Multi-layer printed circuit boards allow for higher component density, because circuit traces on the inner layers would otherwise take up surface space between components. In some implementations, printed circuit board 14 may be a multilayer printed circuit board, e.g., such as a 4-layer, 6-layer, or up to a 10-layer printed circuit board.

Printed circuit board 14 may itself carry one or more processors and/or non-transitory computer readable storage media containing instructions executable by the one or more processors for controlling optical sensor 10. The one or more processors mounted on printed circuit board 14 can control the one or more optical emitters 16 and one or more optical detectors 18 also mounted on the printed circuit board for performing some or all of the functions attributable to optical sensor 10 herein.

In other configurations, such as those described in greater detail below with respect to FIG. 3, printed circuit board 14 that is part of optical sensor 10 may not include any processors. Rather, printed circuit board 14 of optical sensor 10 may include optical emitters 16, optical detectors 18, and any other optional surface mounted components such as resistors, capacitors, and/or inductors without including the hardware performing the processor functions of the optical sensor. In these configurations, optical sensor 10 may be physically and/or electrically coupled to a separate, main circuit board that includes the processor functionality. The main circuit board may include one or more processors that can control one or more optical sensors engaged with the main circuit board, each of which may be configured as described above with respect to optical sensor 10.

This arrangement of components, including the segregation of the one or more processors to the main circuit board, may be useful to create a cost-effective, modular optical sensor system. Each optical sensor 10 used in the optical sensor system may be a comparatively simple, low cost component that can be selectively engaged with the main processor board to then control operation of the sensor(s) engaged there with. This can allow optical sensors having different configurations (e.g., optical emitters 16 that emit at different wavelengths and/or optical detectors 18 that detect different wavelengths) from each other to be selectively engaged with the main circuit board depending on the desired application.

To facilitate modularity and optional engagement with a main circuit board, printed circuit board 14 of optical sensor 10 may include one or more alignment features that are configured to engage with one or more complementary alignment features of a corresponding component, such as a main circuit board. Any physical feature that aligns with a corresponding complementary physical feature to establish relative positioning and/or alignment can be used. In the example of FIG. 1, optical sensor 10 is illustrated as having at least one alignment pin 48, which is illustrated as being implemented with a plurality of alignment pins (specifically three in the illustrated example) projecting actively from printed circuit board 14. Each alignment pin 48 can be received in a corresponding hole configured (e.g., size and/or shaped) to receive the alignment pin. The corresponding hole(s) may be formed in a main circuit board and provide the complementary alignment feature for aligning and/or engaging optical sensor 10 with the main circuit board.

Figure 3:
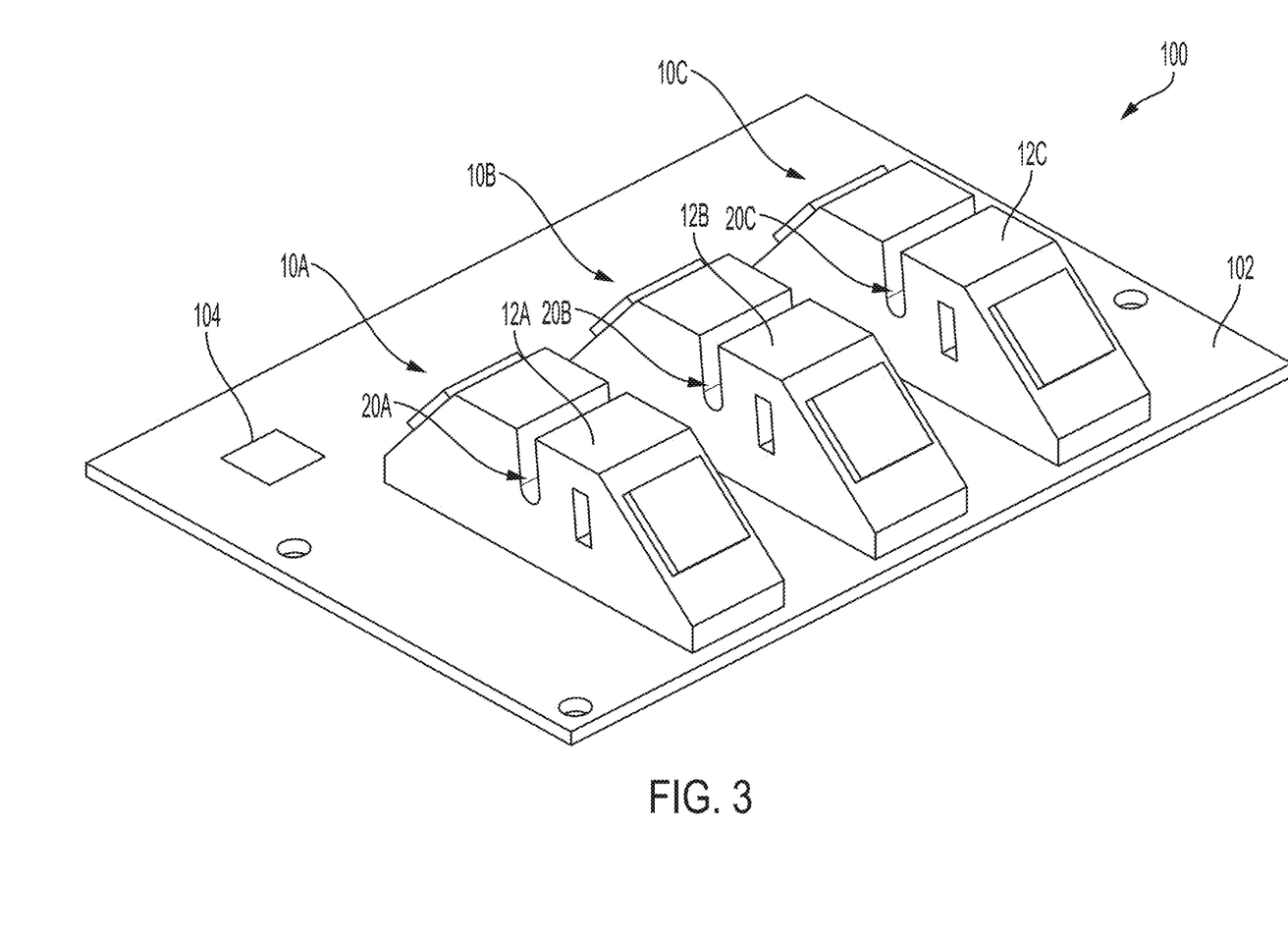
FIG. 3 is a perspective view of an example optical sensor system that can include multiple of the optical sensors of FIGS. 1 and 2.

FIG. 3 is a perspective view of an example optical sensor system 100 that can include multiple optical sensors 10A-10C (collectively referred to as "optical sensors 10") each configured according to the description of optical sensor 10 above with respect to FIGS. 1 and 2. Optical sensor system 100 includes a main printed circuit board 102 carrying one or more processors 104. Optical sensors 10 each include a housing 12, a printed circuit board 14, one or more optical emitters 16 mounted on the printed circuit board, and one or more optical detectors mounted on the printed circuit board, as discussed above. Each of optical sensors 10 can be physically and/or electrically coupled to the main circuit board 102 and the one or more processors 104 carried by the main circuit board. The one or more processors 104 carried by the main circuit board can control each of the optical sensors 10 coupled to the main circuit board.

While one or more of the optical sensors 10 may itself include a processor to control the optical sensor, in other implementations, processor 104 of main circuit board 102 may control each optical sensor 10 coupled to the board. For example, one or more of optical sensors 10 (e.g., optionally all of the optical sensors 10) may not include a processor to control the optical emitter 16 and optical detector of the optical sensor. Rather, processor 104 of main circuit board 102 may be utilized to control the optical emitters and detectors of each of the optical sensors 10, when the optical sensors are coupled to the main circuit board 102. In general, main printed circuit board 102 may have any of the configurations discussed above with respect to printed circuit boards for printed circuit board 14.

In some examples, optical sensors 10 are permanently coupled to main circuit board 102, e.g., such that the optical sensors cannot be removed from the main circuit board without breaking bonding and/or wiring connecting an individual optical sensor to the main circuit board. In other examples, one or more of optical sensors 10 (e.g., optionally all of optical sensors 10) are removably coupled to main circuit board 102. For example, each such optical sensor 10 may be configured to be selectively mechanically and/or electrically connected to the main circuit board and removed therefrom, e.g., without breaking bonding and/or wiring connecting an individual optical sensor to the main circuit board. This arrangement may be useful, for example, to replace individual optical sensors on main circuit board 102. Individual optical sensors may be replaced on main circuit board 102 in the event of a component failure and/or for application specific situations where a different optical sensor is desirable used.

For example, in some applications, each optical sensor 10 that is used in optical sensor system 100 may include one or more optical emitters configured to emit light at a wavelength or range of wavelengths different than each other optical sensor 10 in the system. Similarly, each optical sensor 10 that is used in optical sensor system 100 may include one or more optical detectors configured to detect light at a wavelength or range of wavelengths different than each other optical sensor 10 in the system. This can provide different optical measurements by each optical sensor 10 in the system. In the event that a different set of optical measurements are desired to be made using optical sensor system 10 (e.g., at a different wavelength or range of wavelengths), one or more of optical sensors 10 may be removed from optical sensor system 100 and replace with one or more other optical sensors that emit light and/or detect light at the wavelength(s) desired for the specific application. This can provide a modular, readily adaptable optical sensor system.

Although optical sensor system 100 may be usefully implemented with multiple optical sensors emitting and/or detecting light at different wavelengths or wavelength ranges from each other, the system may also include two or more optical sensors 10 that emit and/or detect light at a same wavelength(s) as each other. This may be useful to provide redundant measurements of the same optical parameter, which may increase the accuracy of the measurement system and alert when there is a component failure providing an inaccurate reading.

Optical sensor system 100 in the example of FIG. 3 is shown as including three optical sensors 10. In other configurations according to the disclosure, the optical sensor system may have fewer optical sensors (e.g., one, two) or more optical sensors (e.g., four, five, or more), and the disclosure is not limited in this respect.

To physically and/or electrically connect an individual optical sensor 10 to main printed circuit board 102, each optical sensor may include an alignment feature configured to engage with a complementary alignment feature on main circuit board 102. For example, printed circuit board 14 of each individual optical sensor 10 may include a pin or hole, and main printed circuit board 102 can include a corresponding hole or pin, respectively, to engage with the feature on the optical sensor.

To electrically couple each individual optical sensor 10 to main printed circuit board 102, each individual optical sensor 10 may include one or more electrodes, wires, and/or other electrical connection features. The electrical connection feature(s) of each individual optical sensor 10 can be physically and/or electrically coupled to corresponding electrical connection features on main printed circuit board 102 to establish electrical communication between the components.

Figure 4:
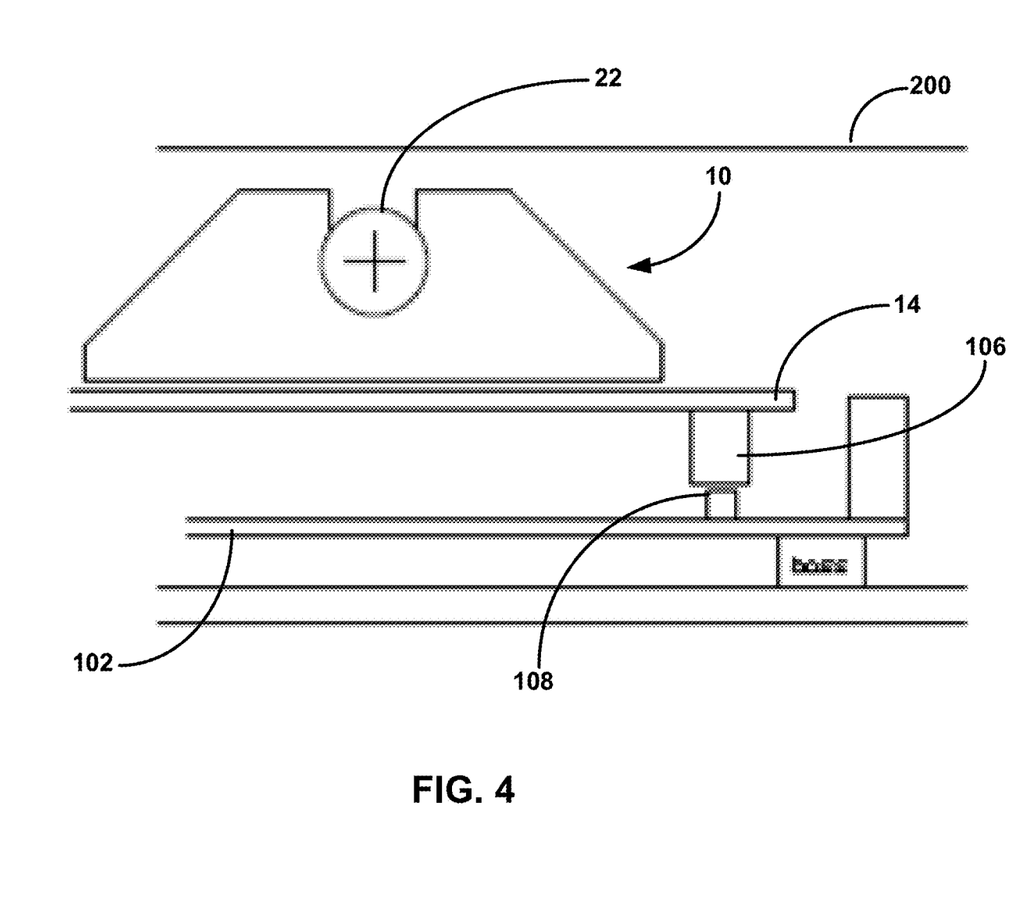
FIG. 4 is a side view of an example electrical connection interface that may be used to connect an individual optical sensor to a main printed circuit board in the example system of FIG. 3.

FIG. 4 is a side view of an example electrical connection interface that may be used to connect an individual optical sensor 10 to main printed circuit board 102. In this example, optical sensor 10 is illustrated as having an electrode 106 projecting from printed circuit board 14. When an alignment feature (e.g., pin 48 in FIG. 1) is inserted into a complementary alignment feature of printed circuit board 102, electrode 106 can engage a counter electrode 108 of main circuit board 102, establish electrical communication between optical sensor 10 and main printed circuit board 102 (in the processor 104 carried by the main printed circuit board). Although FIG. 4 illustrates a single electrode and counter electrode, multiple electrode/counter electrode arrangements may be used. Other electrical connection arrangements may also be used, such as wiring carried by optical sensor 10 that includes a male or female connector, and wiring extending from main printed circuit board 102 with a complementary female or male connector, respectively.

Once optical sensor 10 is physically and/or electrically connected to main circuit board 102, processor 104 carried by the main circuit board may control the optical sensor. For example, processor 104 may send control signals to optical emitter 16 of optical sensor 10 to control the emission of light by the optical emitter into a fluid sample under analysis. Processor 104 may receive signals from optical detector 18 of optical sensor 10 indicative of light detected from the fluid sample under analysis following the controlled emission of light by optical emitters 16. In addition to or in lieu of establishing control communication between main printed circuit board 102 and optical sensor 10, the electrical connection(s) between the components may also establish a power supply to optical sensor 10.

To convey fluid through each of the one or more optical sensors attached to main printed circuit board 102, transparent tubing line 22 can be routed through the channels 20 of each of the optical sensors. Each of the plurality of optical sensors 10 may have a different transparent tubing line 22 position in the channel 20 thereof. These different transparent tubing lines 22 may or may not be fluidly connected together, e.g., with one or more intervening sections of tubing. For instance, in one example, multiple tubing lines are routed to optical sensor system 100, with a different one of the multiple tubing lines supplying fluid to a corresponding one of each of the plurality of optical sensors 10. This arrangement may be useful to provide different fluids (e.g., a liquid sample mixed with different reagents) two different optical sensors 10 and/or have a different residence time for the fluid within each optical sensor 10 for optical analysis.

In another example, a single transparent tubing line 22 (which can be formed of and unbroken, unitary section of tubing or multiple different sections of tubing joined together) can be routed in series through the channels 20 of each of the optical sensors 10 forming optical sensor system 100. Fluid flowing through the single transparent tubing line 22 may first pass through channel 20A of optical sensor 10A for optical analysis by that sensor, followed by passing through channel 20B of optical sensor 10B for optical analysis by that sensor, followed by passing through channel 20C of optical sensor 10C for optical analysis by that sensor. To facilitate efficient routing of the single transparent tubing line 22 in these types of configurations, the channels 20 of each of the optical sensors 10 may be co-linearly aligned, as illustrated in the example of FIG. 3. This can allow the continuous length of transparent tubing 22 to extend linearly through the co-linearly aligned channels.

Figure 5:
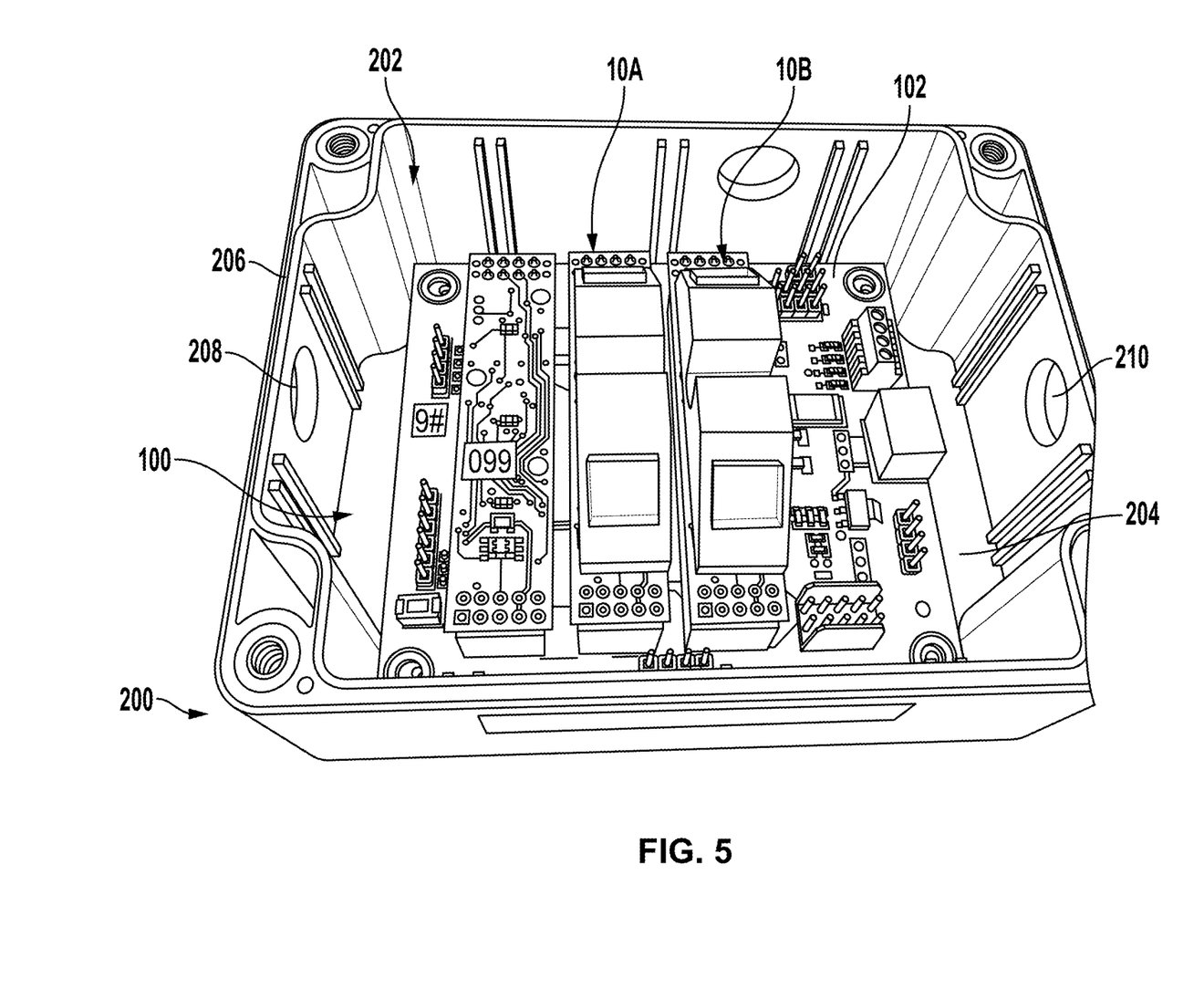
FIG. 5 is a perspective image of an example enclosure for housing optical sensor components.

Whether implemented as a single optical sensor 10 or optical sensor system 100 that includes multiple optical sensors, and optical sensor arrangement according disclosure may be provided in an enclosure that houses the components of the arrangement. FIG. 5 is a perspective illustration of an example enclosure for housing the optical sensor components. As shown, enclosure 200 may define a cavity 202 containing optical sensor 10 and/or optical sensor system 100.

In the illustrated configuration, an optical sensor 100 is shown positioned inside of enclosure 200, including main printed circuit board 102 and a plurality of optical sensors 10 physically and/or electrically coupled to the main circuit board. Enclosure 200 can have a bottom wall 204 and one or more sidewalls 206. A top wall or cover (not illustrated in FIG. 5) may be included to provide a bounded cavity containing the components of the sensor system, which may function to physically protect the components from the ambient environment and/or block interfering ambient light. To allow fluid to enter enclosure 200 for analysis by optical sensors 10, enclosure may include a fluid inlet 208 and a fluid outlet 210. Transparent tubing line 22 may be routed through fluid inlet 208 and fluid outlet 210 (with the fluid line extending through the channels of the one or more optical sensors position in enclosure. In this way, fluid can enter enclosure 200, pass through the channels of each optical sensor 10 for optical analysis by that sensor, and subsequently exit out of the enclosure.

Various devices and systems described herein may include one or more processors. Features described as processors, and control actions and techniques implementable by processor control, may be may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

A circuit board carrying a processor may also carry, and/or be communicatively connected to, a non-transitory computer-readable medium, such as a computer-readable storage medium, containing instructions. Instructions embedded or encoded in a computer-readable storage medium may cause a programmable processor, or other processor, to perform a technique as described in this disclosure, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. An optical sensor comprising:
a housing defining a channel configured to receive a transparent tubing line through which fluid can flow during operation, the housing defining a primary optical pathway transecting the channel, a light emission optical pathway intersecting the primary optical pathway on one side of the channel, and a light detection optical pathway intersecting the primary optical pathway on an opposite side of the channel, wherein the primary optical pathway, the light emission optical pathway, and the light detection optical pathway are each surrounded by an optically opaque material to bound light movement therethrough;
a printed circuit board;
an optical emitter mounted on the printed circuit board; and
an optical detector mounted on the printed circuit board;
wherein the housing is positioned on the printed circuit board with the optical emitter aligned to emit light into the light emission optical pathway and the optical detector aligned to receive light from the light detection optical pathway,
the primary optical pathway, the light emission optical pathway, and the light detection optical pathway are each surrounded by an optically opaque material to bound light movement therethrough,
the light emission optical pathway intersects the primary optical pathway at a first angle causing light traveling linearly through the light emission optical pathway to change direction to travel through the primary optical pathway, and
the light detection optical pathway intersects the primary optical pathway at a second angle causing light traveling linearly through the primary optical pathway to change direction to travel through the light emission optical pathway.

2. The optical sensor of claim 1, further comprising:
a first mirror positioned at an intersection between the light emission optical pathway and the primary optical pathway, the first mirror being configured to reflect light emitted by the optical emitter from the light emission optical pathway into the light detection optical pathway; and
a second mirror positioned at an intersection between the light detection optical pathway and the primary optical pathway, the second mirror being configured to reflect light from the primary optical pathway into the light detection optical pathway for detection by the optical detector.

3. The optical sensor of claim 2, wherein:
the primary optical pathway extends in a direction parallel to a surface of the printed circuit board,
the light emission optical pathway extends orthogonally from the primary optical pathway to the printed circuit board, and
the light detection optical pathway extends orthogonally from the primary optical pathway to the printed circuit board.

4. The optical sensor of claim 2, wherein
the housing defines a trapezoidal shape comprising a top surface, a first lateral side surface, and a second lateral side surface,
the channel extends from the top surface toward the printed circuit board,
the first mirror is bonded to the first lateral side surface, and
the second mirror is bonded to the second lateral side surface.

5. The optical sensor of claim 1, wherein the optical emitter and the optical detector are each surface mounted to the printed circuit board.

6. The optical sensor of claim 1, wherein:
the optical detector comprises a first optical detector and a second optical detector,
the light detection optical pathway comprises a first light detection optical pathway intersecting the primary optical pathway and a second light detection optical pathway intersecting the primary optical pathway, and
the first optical detector is aligned to receive light from the first light detection optical pathway and the second optical detector is aligned to receive light from the second light detection optical pathway.

7. The optical sensor of claim 1, wherein printed circuit board comprises at least one electrical connector configured to electrically connect the printed circuit board to a main printed circuit board and a processor which, when the printed circuit board is electrically connected to the main printed circuit board via the at least one electrical connector, is configured to control the optical emitter and the optical detector.

8. The optical sensor of claim 7, wherein the printed circuit board comprises an alignment feature configured to engage a complementary alignment feature of the main circuit board.

9. An optical sensor system comprising:
a main printed circuit board carrying a processor;
a plurality of optical sensors each comprising:
a housing defining a channel configured to receive a transparent tubing line through which fluid can flow during operation, the housing defining a primary optical pathway transecting the channel, a light emission optical pathway intersecting the primary optical pathway on one side of the channel, and a light detection optical pathway intersecting the primary optical pathway on an opposite side of the channel, wherein the primary optical pathway, the light emission optical pathway, and the light detection optical pathway are each surrounded by an optically opaque material to bound light movement therethrough, the light emission optical pathway intersects the primary optical pathway at a first angle causing light traveling linearly through the light emission optical pathway to change direction to travel through the primary optical pathway, and the light detection optical pathway intersects the primary optical pathway at a second angle causing light traveling linearly through the primary optical pathway to change direction to travel through the light emission optical pathway;
a printed circuit board;
an optical emitter mounted on the printed circuit board; and
an optical detector mounted on the printed circuit board;
the housing being positioned on the printed circuit board with the optical emitter aligned to emit light into the light emission optical pathway and the optical detector aligned to receive light from the light detection optical pathway,
wherein the printed circuit board of each of the plurality of optical sensors is coupled to the main circuit board with the processor carried by the main circuit board being electrically coupled to the optical emitter and optical detector of each of the plurality of optical sensors and configured to control the optical emitter and optical detector of each of the plurality of optical sensors.

10. The optical sensor system of claim 9, wherein the optical emitter of each of the plurality of optical sensors comprises a light emitting diode configured to emit light at a single wavelength or a single wavelength band, and the light emitting diode of each of the plurality of optical sensors is configured to emit light at a wavelength or wavelength band different than each other of the plurality of optical sensors.

11. The optical sensor system of claim 9, wherein the printed circuit board of each of the plurality of optical sensors comprises an alignment feature engaged with a complementary alignment feature of the main circuit board.

12. The optical sensor system of claim 9, wherein the channel defined by the housing of each of the plurality of optical sensors is co-linearly aligned with each other with a continuous length of the transparent tubing extending through the co-linearly aligned channels.

13. The optical sensor system of claim 9, further comprising an enclosure housing the main printed circuit board and each of the plurality of optical sensors, the enclosure having a fluid inlet and a fluid outlet.

14. The optical sensor system of claim 9, wherein the printed circuit board of each of the plurality of optical sensors is removably coupled to the main circuit board to facilitate replacement of any one of the plurality of optical sensors.

15. The optical sensor system of claim 9, wherein each of the plurality of optical sensors further comprises:
a first mirror positioned at an intersection between the light emission optical pathway and the primary optical pathway, the first mirror being configured to reflect light emitted by the optical emitter from the light emission optical pathway into the light detection optical pathway; and
a second mirror positioned at an intersection between the light detection optical pathway and the primary optical pathway, the second mirror being configured to reflect light from the primary optical pathway into the light detection optical pathway for detection by the optical detector.

16. The optical sensor system of claim 15, wherein, for each of the plurality of optical sensors:
the primary optical pathway extends in a direction parallel to a surface of the printed circuit board,
the light emission optical pathway extends orthogonally from the primary optical pathway to the printed circuit board, and
the light detection optical pathway extends orthogonally from the primary optical pathway to the printed circuit board.

17. The optical sensor system of claim 15, wherein, for each of the plurality of optical sensors:
the housing defines a trapezoidal shape comprising a top surface, a first lateral side surface, and a second lateral side surface, the channel extends from the top surface toward the printed circuit board, the first mirror is bonded to the first lateral side surface, and the second mirror is bonded to the second lateral side surface.

18. A method comprising:

flowing a sample through a fluid tubing line extending through a plurality of optical sensors coupled to a main printed circuit board carrying a processor, each of the plurality of optical sensors comprising:

- a housing defining a channel in which the fluid tubing line is positioned, a primary optical pathway transecting the channel, a light emission optical pathway intersecting the primary optical pathway, and a light detection optical pathway intersecting the primary optical pathway on an opposite side of the channel, wherein the primary optical pathway, the light emission optical pathway, and the light detection optical pathway are each surrounded by an optically opaque material to bound light movement therethrough, the light emission optical pathway intersects the primary optical pathway at a first angle causing light traveling linearly through the light emission optical pathway to change direction to travel through the primary optical pathway, and the light detection optical pathway intersects the primary optical pathway at a second angle causing light traveling linearly through the primary optical pathway to change direction to travel through the light emission optical pathway;
- a printed circuit board coupled to the main printed circuit board;
- an optical emitter mounted on the printed circuit board; and
- an optical detector mounted on the printed circuit board;

controlling, by the processor, the optical emitter of each of the plurality of optical sensors to emit light into the sample via the light emission optical pathway and the primary optical pathway; and controlling, by the processor, the optical detector of each of the plurality of optical sensors to detect light from the sample via the primary optical pathway and the light detection optical pathway.

19. The method of claim 18, wherein controlling, by the processor, the optical detector of each of the plurality of optical sensors to detect light from the sample comprises controlling, the optical detector of at least one of plurality of optical sensors to detect light emitted from the optical emitter and passing through the sample, thereby providing an absorbance measurement of the sample.

20. The method of claim 18, wherein each of the plurality of optical sensors further comprises:

- a first mirror positioned at an intersection between the light emission optical pathway and the primary optical pathway, the first mirror being configured to reflect light emitted by the optical emitter from the light emission optical pathway into the light detection optical pathway; and
- a second mirror positioned at an intersection between the light detection optical pathway and the primary optical pathway, the second mirror being configured to reflect light from the primary optical pathway into the light detection optical pathway for detection by the optical detector.

\* \* \* \* \*